United States Patent
Ogihara

(10) Patent No.: US 10,524,989 B2
(45) Date of Patent: Jan. 7, 2020

(54) LIQUID COMPOSITION FOR ORAL CAVITY CONTAINED IN FOAM-DISCHARGING CONTAINER

(71) Applicant: KAO CORPORATION, Tokyo (JP)

(72) Inventor: Aya Ogihara, Koto-ku (JP)

(73) Assignee: KAO CORPORATION, Tokyo (JP)

( * ) Notice: Subject to any disclaimer, the term of this patent is extended or adjusted under 35 U.S.C. 154(b) by 213 days.

(21) Appl. No.: 15/539,914

(22) PCT Filed: Dec. 25, 2015

(86) PCT No.: PCT/JP2015/086290
§ 371 (c)(1),
(2) Date: Jun. 26, 2017

(87) PCT Pub. No.: WO2016/107730
PCT Pub. Date: Jun. 30, 2016

(65) Prior Publication Data
US 2018/0015008 A1  Jan. 18, 2018

(30) Foreign Application Priority Data
Dec. 26, 2014 (JP) ................................ 2014-264069

(51) Int. Cl.
*A61K 8/04* (2006.01)
*A61K 8/44* (2006.01)
*A61Q 11/00* (2006.01)
*A61K 8/34* (2006.01)
*A61K 8/46* (2006.01)

(52) U.S. Cl.
CPC .............. *A61K 8/046* (2013.01); *A61K 8/345* (2013.01); *A61K 8/44* (2013.01); *A61K 8/442* (2013.01); *A61K 8/463* (2013.01); *A61K 8/466* (2013.01); *A61Q 11/00* (2013.01); *A61K 2800/74* (2013.01); *A61K 2800/87* (2013.01); *A61K 2800/92* (2013.01)

(58) Field of Classification Search
None
See application file for complete search history.

(56) References Cited

U.S. PATENT DOCUMENTS

2008/0038210 A1* 2/2008 Yano ................. A61K 8/24
424/49

FOREIGN PATENT DOCUMENTS

| JP | 8-333226 A | 12/1996 |
|----|-----------|---------|
| JP | 9-295923 A | 11/1997 |
| JP | 10-87457 A | 4/1998 |
| JP | 10-114637 A | 5/1998 |
| JP | 10-167943 A | 6/1998 |
| JP | 11-130647 A | 5/1999 |
| JP | 2000-44448 A | 2/2000 |
| JP | 2007-137773 A | 6/2007 |
| JP | 2009-155218 A | 7/2009 |
| JP | 2014-141471 A | 8/2014 |

OTHER PUBLICATIONS

International Search Report dated Mar. 15, 2016 in PCT/JP2015/086290 filed Dec. 25, 2015.
Extended European Search Report dated Jul. 12, 2018 in Patent Application No. 15873298.2, citing document AO therein, 8 pages.

* cited by examiner

*Primary Examiner* — Nannette Holloman
(74) *Attorney, Agent, or Firm* — Oblon, McClelland, Maier & Neustadt, L.L.P.

(57) ABSTRACT

The present invention relates to a liquid composition for oral cavity contained in a foam-discharging container, which enables effective suppression of an increase in viscosity at a low temperature and has high storage stability, while retaining good foam quality.
The present invention provides a liquid composition for oral cavity contained in a foam-discharging container, comprising the following components (A), (B) and (C):
(A) 0.3 mass % or more and 2.5 mass % or less in total of one or more surfactants selected from the group consisting of an anionic surfactant (a-1) selected from the group consisting of an N-acylamino acid salt, an alkyl sulfate ester salt, an alkyl phosphate salt and an α-olefin sulfonate salt, and an amphoteric surfactant (a-2);
(B) 10 mass % or more and 40 mass % or less in total of one or more polyols selected from the group consisting of glycerin, propylene glycol, butylene glycol, and polyethylene glycol having an average molecular weight of 1,000 or less; and
(C) 50 mass % or more and 89 mass % or less of water;
wherein
a content of the component (a-1) is 1.2 mass % or less, or the component (a-1) is not comprised, and a content of the component (a-2) is 0.25 mass % or more and 1.5 mass % or less, and furthermore, contents of ethanol, an abrasive powder, a binder and a nonionic surfactant, and a sugar alcohol which is a solid at 20° C. are restricted in specified ranges.

10 Claims, No Drawings

LIQUID COMPOSITION FOR ORAL CAVITY CONTAINED IN FOAM-DISCHARGING CONTAINER

CROSS REFERENCE TO RELATED APPLICATIONS

This application is a national stage entry under 35 USC 371 of PCT/JP2015/086290 filed on Dec. 25, 2015, and claims priority to Japanese Patent Application No. 2014-264069 filed on Dec. 26, 2014.

FIELD OF THE INVENTION

The present invention relates to a liquid composition for oral cavity contained in a foam-discharging container.

BACKGROUND OF THE INVENTION

It has been conventionally known that a liquid composition for oral cavity is filled in a container which enables discharging the content in the form of foam, thereby directly applying a foam composition to the oral cavity through a discharge port upon use to provide feeling of use and the like characteristic of such foam. Various surfactants are used in such a composition in order to achieve desired performances.

For example, in Patent Literature 1, a liquid agent for oral cavity containing dextranase and a nonionic surfactant such as polyoxyethylene hardened castor oil is directly injected into the mouth at a specified foam density to result in an increase in retaining property of the dextranase in the plaque. In addition, Patent Literature 2 discloses an agent for oral cavity obtained by filling a liquid composition for oral cavity containing an anionic surfactant such as phosphate monoesters into a container, and the composition is directly applied in the form of foam with the intention of enhancing usability and the like.

Furthermore, Patent Literatures 3 to 4 disclose a foam composition for oral cavity filled into a non-gas normal pressure container, the composition containing an anionic surfactant, a nonionic surfactant or an amphoteric surfactant in each specified amount, which intends to improve dispersibility, foam quality and the like in the oral cavity.

(Patent Literature 1) JP-A-2000-44448
(Patent Literature 2) JP-A-10-167943
(Patent Literature 3) JP-A-08-333226
(Patent Literature 4) JP-A-09-295923

SUMMARY OF THE INVENTION

The present invention relates to a liquid composition for oral cavity contained in a foam-discharging container, comprising the following components (A), (B) and (C):

(A) 0.3 mass % or more and 2.5 mass % or less in total of one or more surfactants selected from the group consisting of an anionic surfactant (a-1) selected from the group consisting of an N-acylamino acid salt, an alkyl sulfate ester salt, an alkyl phosphate salt and an α-olefin sulfonate salt, and an amphoteric surfactant (a-2);

(B) 10 mass % or more and 40 mass % or less in total of one or more polyols selected from the group consisting of glycerin, propylene glycol, butylene glycol, and polyethylene glycol having an average molecular weight of 1,000 or less; and (C) 50 mass % or more and 89 mass % or less of water; wherein a content of the component (a-1) is 1.2 mass % or less, or the component (a-1) is not comprised, and a content of the component (a-2) is 0.25 mass % or more and 1.5 mass % or less; and furthermore, a content of ethanol is 3 mass % or less, a content of an abrasive powder is 0.5 mass % or less, a content of a binder is 0.3 mass % or less, a content of a nonionic surfactant is 1.2 mass % or less, and a content of a sugar alcohol which is a solid at 20° C. is 5 mass % or less.

The present invention also relates to a method of using the liquid composition for oral cavity contained in a foam-discharging container, comprising directly discharging the liquid composition for oral cavity contained in a foam-discharging container, into the oral cavity through a discharge port provided in the foam-discharging container, to apply the liquid composition for oral cavity contained in a foam-discharging container, which has gone through the discharge port, in the form of foam into the oral cavity.

If only a nonionic surfactant is used as a surfactant as in Patent Literature 1, foam may be difficult to be favorably retained in the oral cavity where saliva is also present. In addition, even when an anionic surfactant is used as in Patent Literature 2, a large amount of ethanol contained easily causes defoaming and also probably causes clogging in a porous member provided in a foam-discharging container. Furthermore, even if an anionic surfactant is combined with a nonionic surfactant or an amphoteric surfactant as in Patent Literature 3 to 4, viscosity of the composition may rapidly increase due to the contents of such surfactants and the contents of other components such as ethanol when the composition is preserved at a low temperature, resulting in deterioration in dischargeability from the container, and therefore there is still room for improvement.

Accordingly, the present invention relates to a liquid composition for oral cavity contained in a foam-discharging container, which enables effective suppression of an increase in viscosity at a low temperature and has high storage stability, while retaining good foam quality.

The present inventor made various studies, and found that when limited amount(s) of one or more surfactants selected from the group consisting of a specified anionic surfactant and an amphoteric surfactant are used as a surfactant, specified amounts of a specified polyol and water are used in combination therewith, and the contents of ethanol, an abrasive powder, a binder, a nonionic surfactant and a specified sugar alcohol are limited, there can be provided a liquid composition for oral cavity contained in a foam-discharging container, which provides good foam quality, enables suppression of an increase in viscosity to thereby have good dischargeability even after storage at a low temperature and also exhibits excellent storage stability.

The liquid composition for oral cavity contained in a foam-discharging container of the present invention not only can provide good foam quality even when saliva is present, and can exhibit excellent feeling of use, when applied to the oral cavity from the container in the form of foam upon use; but also can exhibit high storage stability while retaining a proper viscosity and retaining good dischargeability, even after storage at a low temperature, and can exhibit good dischargeability even after storage at a high temperature. Furthermore, adsorption of a bactericide in the oral cavity can also be promoted and an improvement of the oral cavity environment can be effectively achieved.

DETAILED DESCRIPTION OF THE INVENTION

Hereinafter, the present invention is described in detail.

The liquid composition for oral cavity contained in a foam-discharging container of the present invention comprises 0.3 mass % or more and 2.5 mass % or less in total of one or more surfactants selected from the group consisting of an anionic surfactant (a-1) selected from a N-acylamino acid salt, an alkyl sulfate ester salt, an alkyl phosphate salt and an α-olefin sulfonate salt, and an amphoteric surfactant (a-2), as a component (A); and the content of the component (a-1) is 1.2 mass % or less, or the component (a-1) is not comprised, and the content of the component (a-2) is 0.25 mass % or more and 1.5 mass % or less. That is, in the liquid composition for oral cavity contained in a foam-discharging container of the present invention, the surfactant as the component (A) is one or more selected from the group consisting of the anionic surfactant (a-1) selected from the group consisting of a N-acylamino acid salt, an alkyl sulfate ester salt, an alkyl phosphate salt and an α-olefin sulfonate salt, and the amphoteric surfactant (a-2), and the total content thereof is 0.3 mass % or more and 2.5 mass % or less; when the amphoteric surfactant as the component (a-2) is contained in an amount of 0.25 mass % or more and 1.5 mass % or less, the anionic surfactant as the component (a-1) may not be contained; and when the anionic surfactant as the component (a-1) is contained in an amount of 1.2 mass % or less, the amphoteric surfactant as the component (a-2) may be contained in an amount of 0.25 mass % or more and 1.5 mass % or less together with the component (a-1). Thus, when the liquid composition for oral cavity comprises the surfactant as the component (A) in a limited amount, inclusion of the restricted amount of the anionic surfactant as the component (a-1), which can provide good foam quality while easily generating a precipitate under a low-temperature environment, and further inclusion of a specified amount of the amphoteric surfactant as the component (a-2) in combination can effectively suppress generation of a precipitate from the component (a-1), as well as can retain a proper viscosity to enhance dischargeability from the container and feeling of use even after low-temperature storage, and to exhibit excellent low-temperature storage stability.

In other words, the liquid composition for oral cavity contained in a foam-discharging container of the present invention is a composition to be applied into the oral cavity unlike a skin cleanser such as a hand soap, a face wash, a body cleanser and a shampoo, and therefore must be reduced in harm and stimulation resulting from not only an anionic surfactant and an amphoteric surfactant, but also a cationic bactericide to be used if necessary, and the composition is thus restricted with respect to inclusion of such surfactants. The liquid composition for oral cavity contained in a foam-discharging container of the present invention, in which inclusion of the anionic surfactant and the amphoteric surfactant is thus restricted, preferably has a proper foam viscosity so that foam discharged from the container is favorably extended, and thus not only allows the foam to be smoothly spread in the oral cavity environment where saliva is present, but also enables the foam to be favorably maintained due to viscous property resulting from a proper foam viscosity even when the foam is diluted with saliva. While the liquid composition for oral cavity contained in a foam-discharging container of the present invention enables suppression of an increase in liquid viscosity even at a low temperature, the liquid composition can provide a high density of the foam discharged from the container to thereby not only achieve good dischargeability, but also achieve good quality of foam which can spread in the oral cavity and be retained well.

Examples of one or more anionic surfactants selected from the group consisting of a N-acylamino acid salt, an alkyl sulfate ester salt, an alkyl phosphate salt and an α-olefin sulfonate salt as the component (a-1) includes acylsarcosine salts such as an N-lauroylsarcosine salt and an N-myristoylsarcosine salt; N-methyl acyl taurine salts such as an N-lauroyl methyl taurine salt and an N-myristoyl methyl taurine salt; N-acyl taurine salts such as an N-lauroyl taurine salt and an N-myristoyl taurine salt; N-acylglutamic acid salts such as an N-lauroylglutamic acid salt, an N-myristoylglutamic acid salt, an N-palmitoylglutamic acid salt and an N-cocoylglutamic acid salt; alkyl sulfate ester salts such as lauryl sulfate and myristyl sulfate; alkyl phosphate salts such as a lauryl phosphate salt; and α-olefin (C14 to 16) sulfonate salts having an olefin having 14 to 16 carbon atoms.

Among them, the anionic surfactant as the component (a-1) preferably is one or more selected from the group consisting of an N-lauroylsarcosine salt, an N-lauroyl methyl taurine salt, an N-lauroyl taurine salt, an N-myristoyl-L-glutamic acid salt, an N-lauroylglutamic acid salt, a lauryl sulfate salt, a lauryl phosphate salt and an α-olefin (C14 to 16) sulfonate salt in terms of foaming property and detergency as well as stability, more preferably one or more selected from the group consisting of an N-lauroyl methyl taurine salt, an N-myristoylglutamic acid salt and a lauryl sulfate salt in terms of easy foam rinsability, or bactericidal property or wettability upon application into the oral cavity, and such a salt is preferably an alkali metal salt, more preferably a sodium salt or a potassium salt, further preferably a sodium salt. The anionic surfactant as the component (a-1) is preferably one including at least sodium lauryl sulfate in terms of foaming property.

The content of the component (a-1) in the liquid composition for oral cavity contained in a foam-discharging container of the present invention is 1.2 mass % or less, preferably 1 mass % or less, more preferably 0.8 mass % or less, and preferably 0.1 mass % or more, more preferably 0.2 mass % or more, or the anionic surfactant as the component (a-1) is not contained while the component (a-2) is contained, in terms of effectively suppressing generation of a precipitate at a low temperature when comprising the component (a-1) and retaining good foam quality in the oral cavity. The content of the component (a-1) in the liquid composition for oral use contained in a foam-discharging container of the present invention is 1.2 mass % or less, preferably 0.1 mass % or more and 1.2 mass % or less, more preferably from 0.2 to 1 mass %, further preferably from 0.2 to 0.8 mass %, or the component (a-1) is not contained.

The liquid composition for oral cavity contained in a foam-discharging container of the present invention preferably does not contain a fatty acid or a salt thereof as an anionic surfactant other than the component (a-1). Examples of the fatty acid or salt thereof include coconut oil fatty acid, myristic acid, lauric acid, palmitic acid, stearic acid and mixtures thereof, or salts thereof. The content of the fatty acid or salt thereof in the liquid composition for oral cavity contained in a foam-discharging container of the present invention is preferably 0.2 mass % or less, more preferably 0.1 mass % or less, further preferably 0.01 mass % or less, and preferably more than 0 mass %, or further preferably the fatty acid or salt thereof is not contained, in view of ensuring dischargeability from the container, suppressing an increase in viscosity at a low temperature, also effectively suppressing generation of a precipitate, and enhancing the flavor.

While the liquid composition for oral cavity contained in a foam-discharging container of the present invention may contain an anionic surfactant other than the component (a-1) and the fatty acid or salt thereof, the content of the anionic surfactant is preferably lower than the content of the component (a-1) in view of reducing stimulation in the oral cavity or the like to thereby enhance feeling of use, and achieving dischargeability from the container. Examples of the anionic surfactant other than the component (a-1) and the fatty acid or salt thereof include sodium dodecylbenzenesulfonate, α-sulfofatty acid alkyl ester/sodium, a higher fatty acid sulfonated monoglyceride salt, sodium hydrogenated coconut fatty acid monoglyceride monosulfate and sodium lauryl sulfoacetate. The content of the anionic surfactant in the liquid composition for oral cavity contained in a foam-discharging container of the present invention is specifically preferably 0.2 mass % or less, more preferably 0.1 mass % or less, further preferably 0.05 mass % or less, and preferably more than 0 mass %, or further preferably the anionic surfactant other than the component (a-1) and the fatty acid or salt thereof is not contained. Among them, preferably, sodium dodecylbenzenesulfonate, α-sulfofatty acid alkyl ester/sodium and a higher fatty acid sulfonated monoglyceride salt are not contained in view of the solubility in a liquid formulation and suppression of a precipitate.

Examples of the amphoteric surfactant as the component (a-2) include one or more selected from the group consisting of acetic acid betaine such as lauryl dimethylaminoacetic acid betaine; imidazolinium betaine such as 2-alkyl-N-carboxymethyl-N-hydroxyethyl-N-imidazolium betaine; alkyl sulfobetaine such as lauryl sulfobetaine and lauryl hydroxy sulfobetaine; coconut oil fatty acid amide alkyl betaine such as coconut oil fatty acid amide propyl betaine; and long-chain alkyl imidazoline betaine salts such as sodium N-alkyl-1-hydroxyethylimidazoline betaine. Among them, the component (a-2) preferably is one or more selected from the group consisting of coconut oil fatty acid amide alkyl betaine and alkyl sulfobetaine, more preferably coconut oil fatty acid amide alkyl betaine, further preferably coconut oil fatty acid amide alkyl betaine having alkyl having 2 to 5 carbon atoms, further more preferably coconut oil fatty acid amide propyl betaine, in view that, when the component (a-1) is contained, generation of a precipitate at a low temperature is effectively suppressed.

The content of the component (a-2) in the liquid composition for oral cavity contained in a foam-discharging container of the present invention is 0.25 mass % or more, preferably 0.3 mass % or more, more preferably 0.4 mass % or more, in view of effectively suppressing generation of a precipitate at a low temperature even when the liquid composition for oral cavity contained in a foam-discharging container of the present invention comprises the component (a-1), and retaining a proper viscosity after low-temperature storage. In addition, the content of the component (a-2) in the liquid composition for oral cavity contained in a foam-discharging container of the present invention is 1.5 mass % or less, preferably 1.2 mass % or less, more preferably 1 mass % or less, in view of ensuring good foam quality and flavor while preventing generation of a precipitate at a low temperature and suppressing an increase in viscosity at a low temperature. The content of the component (a-2) is then 0.25 mass % or more and 1.5 mass % or less, preferably from 0.3 to 1.2 mass %, more preferably from 0.3 to 1 mass %, further preferably from 0.4 to 1 mass %.

The total content of one or more surfactants selected from the group consisting of the component (a-1) and the component (a-2), as the component (A), in the liquid composition for oral cavity contained in a foam-discharging container of the present invention is 0.3 mass % or more, preferably 0.4 mass % or more, more preferably 0.5 mass % or more, further preferably 0.6 mass % or more, in view of ensuring good foam quality in the oral cavity where saliva is also present. In addition, the total content of one or more surfactants selected from the group consisting of the component (a-1) and the component (a-2), as the component (A), in the liquid composition for oral cavity contained in a foam-discharging container of the present invention is 2.5 mass % or less, preferably 2.2 mass % or less, more preferably 2 mass % or less, further preferably 1.7 mass % or less, further more preferably 1.3 mass % or less, in view of effectively ensuring good taste and feeling of use in the oral cavity, and enhancing adsorption of a specified bactericide such as isopropylmethylphenol or a specified anti-inflammatory agent as described below in the oral cavity when the liquid composition for oral cavity contained in a foam-discharging container of the present invention contains such a bactericide or agent. The total content of one or more surfactants selected from the group consisting of the component (a-1) and the component (a-2), as the component (A), in the liquid composition for oral cavity contained in a foam-discharging container of the present invention is then 0.3 mass % or more and 2.5 mass % or less. In addition, the total content of the surfactant(s) of the component (A) is preferably from 0.4 to 2.2 mass %, more preferably from 0.5 to 2 mass %, further preferably from 0.6 to 1.7 mass %, further more preferably from 0.6 to 1.3 mass % from the same viewpoint.

When the liquid composition for oral cavity contained in a foam-discharging container of the present invention comprises the component (a-1), the mass ratio of the component (a-2) to the component (a-1), (a-2)/(a-1), is preferably 0.5 or more, more preferably 0.55 or more, further preferably 0.6 or more, further more preferably 0.65 or more in view of enhancing low-temperature preservation stability while effectively suppressing generation of a precipitate at a low temperature and retaining a proper viscosity. In addition, the mass ratio of the component (a-2) to the component (a-1), (a-2)/(a-1), is preferably 3 or less, more preferably 2.5 or less, further preferably 2 or less, further more preferably 1.8 or less, still more preferably 1.3 or less, in view of retaining good foam quality and ensuring excellent dischargeability from the container and foam viscosity. The mass ratio of the component (a-2) to the component (a-1), (a-2)/(a-1), is then preferably from 0.5 to 3, more preferably from 0.55 to 2.5, further preferably from 0.6 to 2, further more preferably from 0.65 to 1.8, still more preferably from 0.65 to 1.3.

The liquid composition for oral cavity contained in a foam-discharging container of the present invention comprises 10 mass % or more and 40 mass % or less in total of one or more polyols selected from the group consisting of glycerin, propylene glycol, butylene glycol, and polyethylene glycol having an average molecular weight of 1,000 or less, as a component (B). Thus, good foam quality, and excellent storage stability at a low temperature can be effectively satisfied. Among them, one or more polyols selected from the group consisting of glycerin, propylene glycol and butylene glycol are preferably used as the component (B). Herein, the average molecular weight of the polyethylene glycol means the mass average molecular weight measured by GPC (gel permeation chromatography).

The mass average molecular weight of the polyethylene glycol for use as the component (B) is 1,000 or less, preferably 850 or less in view of low-temperature storage stability and prevention of clogging in a porous member of the foam-discharging container, and is preferably 200 or more, more preferably 400 or more in view of good foam quality.

The total content of the component (B) in the liquid composition for oral cavity contained in a foam-discharging container of the present invention is 10 mass % or more, preferably 12 mass % or more, more preferably 15 mass % or more in view of, while retaining a proper viscosity, enhancing storage stability after low-temperature storage, and also enhancing adsorption of a specified bactericide such as isopropylmethylphenol or a specified anti-inflammatory agent as described below in the oral cavity when the liquid composition for oral cavity contained in a foam-discharging container of the present invention contains such a bactericide or agent. In addition, the total content of the component (B) in the liquid composition for oral cavity contained in a foam-discharging container of the present invention is 40 mass % or less, preferably 37 mass % or less, more preferably 35 mass % or less, further preferably 32 mass % or less, in view of ensuring good dischargeability from the container and excellent feeling of use, suppressing an increase in viscosity, and enhancing low-temperature storage stability. The total content of the component (B) in the liquid composition for oral cavity contained in a foam-discharging container of the present invention is then 10 mass % or more and 40 mass % or less, preferably from 12 to 37 mass %, more preferably from 15 to 35 mass %, further preferably from 15 to 32 mass %. The content of the polyethylene glycol having an average molecular weight of 1,000 or less for use as the component (B) in the liquid composition for oral cavity contained in a foam-discharging container of the present invention is preferably 7 mass % or less, more preferably 5 mass % or less, further preferably 3 mass % or less, further more preferably 2 mass % or less, or such polyethylene glycol may not be contained, in view of a proper viscosity after low-temperature storage.

The mass ratio of the component (B) to the component (A), (B)/(A), is preferably 6 or more, more preferably 8 or more, further preferably 10 or more, further more preferably 12 or more, in view of ensuring good foam quality and also good dischargeability from the container. In addition, the mass ratio of the component (B) to the component (A), (B)/(A), is preferably 130 or less, more preferably 90 or less, further preferably 70 or less, further more preferably 55 or less, further more preferably 52 or less, in view of satisfying both of a proper viscosity after low-temperature storage and storage stability, and enhancing adsorption of a specified bactericides such as isopropylmethylphenol or a specified anti-inflammatory agent as described below in the oral cavity, when the liquid composition for oral cavity contained in a foam-discharging container of the present invention contains such a bactericide or agent. The mass ratio between the component (B) to the component (A), (B)/(A), is then preferably from 6 to 130, more preferably from 8 to 90, further preferably from 8 to 70, further more preferably from 10 to 55, further more preferably from 12 to 52.

The liquid composition for oral cavity contained in a foam-discharging container of the present invention comprises 50 mass % or more and 89 mass % or less of water as a component (C). The water as the component (C) in the present invention means the whole water contained in the liquid composition for oral cavity, including not only purified water, ion-exchange water and the like blended in the liquid composition for oral cavity contained in a foam-discharging container, but also water included in each component blended. Inclusion of such water as the component (C) allows excellent storage stability at a low temperature to be effectively ensured, with good shape retainability being kept and each component being favorably dispersed or dissolved to be favorably diffused in the oral cavity.

The content of the component (C) in the liquid composition for oral cavity contained in a foam-discharging container of the present invention is 50 mass % or more, preferably 55 mass % or more, more preferably 60 mass % or more, further preferably 65 mass % or more, in view of ensuring excellent storage stability at a low temperature and suppressing an increase in viscosity. In addition, the content of the component (C) in the liquid composition for oral cavity contained in a foam-discharging container of the present invention is 89 mass % or less, preferably 86 mass % or less, more preferably 83 mass % or less, in view of retaining good foam quality and dischargeability from the container, and enhancing adsorption of a specified bactericide such as isopropylmethylphenol or a specified anti-inflammatory agent as described below in the oral cavity when the liquid composition for oral cavity contained in a foam-discharging container of the present invention contains such a bactericide or agent. The content of the component (C) in the liquid composition for oral cavity contained in a foam-discharging container of the present invention is then 50 mass % or more and 89 mass % or less, preferably from 55 to 86 mass %, more preferably from 60 to 83 mass %, further preferably from 65 to 83 mass %.

The mass ratio of the component (A) to the component (C), ((A)/(C)), is preferably $0.5\times10^{-2}$ or more, more preferably $0.6\times10^{-2}$ or more, further preferably $0.75\times10^{-2}$ or more, further more preferably $0.8\times10^{-2}$ or more, in view of ensuring sufficiently high foam viscosity and good foam quality and preventing generation of a precipitate at a low temperature. In addition, the mass ratio of the component (A) to the component (C), (A)/(C), is preferably $5\times10^{-2}$ or less, more preferably $4.4\times10^{-2}$ or less, further preferably $2.5\times10^{-2}$ or less, further more preferably $2\times10^{-2}$ or less, in view of effectively suppressing an increase in viscosity at a low temperature and preventing generation of a precipitate after low-temperature storage. The mass ratio of the component (A) to the component (C), (A)/(C), is then preferably from $0.5\times10^2$ to $5\times10^{-2}$, more preferably from $0.6\times10^{-2}$ to $4.4\times10^{-2}$, further preferably from $0.75\times10^{-2}$ to $2.5\times10^{-2}$, further more preferably from $0.8\times10^{-2}$ to $2\times10^{-2}$.

The liquid composition for oral cavity contained in a foam-discharging container of the present invention is preferably transparent or semitransparent. Specifically, no precipitate is preferably present, thereby enabling to prevent an increase in pushing force of the foam-discharging container and to prevent clogging in the porous member of the foam-discharging container. The term "transparent" in the present invention means that the transmittance of light having an absorption wavelength of 550 nm is 80% or more when the oral cavity use liquid composition is filled into a cell having an optical path length of 10 mm, and such a transmittance is further preferably 90% or more, still preferably 95% or more in view of a higher transparency. A quartz cell is here used as the cell.

The content of ethanol in the liquid composition for oral cavity contained in a foam-discharging container of the present invention is 3 mass % or less. The content of ethanol can be thus restricted, thereby effectively suppressing an increase in viscosity at a low temperature, to prevent an excessive increase in pushing force of the foam-discharging container to ensure good dischargeability from the container, and also to prevent generation of a precipitate after low-temperature storage. The content of ethanol in the liquid composition for oral cavity contained in a foam-discharging container of the present invention is 3 mass % or less in view of effectively enhancing the preservation stability at a low temperature and ensuring good dischargeability as described above. The content of ethanol is preferably 2.5 mass % or less, more preferably 2 mass % or less, further preferably 1 mass % or less, and preferably more than 0 mass %, or the liquid composition for oral cavity contained in a foam-discharging container of the present invention preferably does not contain ethanol, in view of preventing deterioration in dischargeability with respect to each repetition of use and storage. In addition, the content of ethanol in the liquid composition for oral cavity contained in a foam-discharging container of the present invention is 3 mass % or less, preferably from 0 to 3 mass %, more preferably from 0 to 2.5 mass %, further preferably from 0 to 2 mass %, still further preferably from 0 to 1 mass %, or the liquid composition for oral cavity contained in a foam-discharging container of the present invention preferably does not comprise ethanol.

When the liquid composition for oral cavity contained in a foam-discharging container of the present invention comprises the anionic surfactant as the component (a-1) and ethanol, the mass ratio of such ethanol to the component (a-1), ethanol/(a-1), is preferably 15 or less, more preferably 10 or less, further preferably 8 or less in view of effectively suppressing an increase in viscosity at a low temperature.

The content of the abrasive powder in the liquid composition for oral cavity contained in a foam-discharging container of the present invention is 0.5 mass % or less. The content of the abrasive powder can be thus restricted to thereby ensure good dischargeability from the container and also effectively enhance storage stability at a low temperature. Examples of such an abrasive powder include one or more selected from the group consisting of light calcium carbonate, heavy calcium carbonate, zeolite, abrasive silica having an oil absorption of 50 to 150 mL/100 g, dicalcium phosphate, tricalcium phosphate, insoluble sodium metaphosphate, aluminum hydroxide, magnesium phosphate, calcium pyrophosphate and magnesium carbonate.

The oil absorption here represents the amount of oil which can be supported by the silica, and is specified by the amount of boiled linseed oil absorbed, as measured according to the method based on JIS K5101-13-2 (established in 2004) as the measurement method.

The content of the abrasive powder in the liquid composition for oral cavity contained in a foam-discharging container of the present invention is 0.5 mass % or less, preferably 0.4 mass % or less, more preferably 0.3 mass % or less, and preferably more than 0 mass %, or the liquid composition for oral cavity contained in a foam-discharging container of the present invention preferably does not comprise the abrasive powder, in view of ensuring good dischargeability from the container and also low-temperature storage stability. In addition, the content of the abrasive powder in the liquid composition for oral cavity contained in a foam-discharging container of the present invention is 0.5 mass % or less, preferably from 0 to 0.5 mass %, more preferably from 0 to 0.4 mass %, further preferably from 0 to 0.3 mass %, or the liquid composition for oral cavity contained in a foam-discharging container of the present invention preferably does not comprise the abrasive powder.

The content of the binder in the liquid composition for oral cavity contained in a foam-discharging container of the present invention is 0.3 mass % or less. The content of the binder can be thus restricted, thereby favorably retaining dischargeability from the container to ensure excellent feeling of use, and also effectively suppressing an increase in viscosity at a low temperature to enhance low-temperature storage stability. Examples of the binder include one or more selected from the group consisting of sodium alginate, carboxymethylcellulose or a salt thereof, carrageenan, xanthan gum, sodium polyacrylate, hydroxyethylcellulose, hydroxypropylcellulose, pectin, tragacanth gum, Arabic gum, guar gum, karaya gum, locust bean gum, gellan gum, tamarind gum, psyllium seed gum, polyvinyl alcohol, sodium chondroitin sulfate and a methoxyethylene-maleic anhydride copolymer. Among them, the binder to be used preferably is one or more selected from the group consisting of carboxymethylcellulose or a salt thereof having a degree of etherification of 0.7 to 2.0, hydroxyethylcellulose, carrageenan and xanthan gum, more preferably a combination of two or more thereof, in view of enhancing the foam viscosity of the liquid composition for oral cavity discharged from the foam-discharging container to favorably keep foam in the presence of saliva in the oral cavity.

The content of the binder in the liquid composition for oral cavity contained in a foam-discharging container of the present invention is 0.3 mass % or less, preferably 0.28 mass % or less, more preferably 0.25 mass % or less in view of ensuring good dischargeability from the container and also storage stability at a low temperature, and is preferably 0.05 mass % or more, more preferably 0.1 mass % or more in view of enhancing foam viscosity to ensure good foam quality and feeling of use, or the liquid composition for oral cavity contained in a foam-discharging container of the present invention may not comprise the binder.

The content of the nonionic surfactant in the liquid composition for oral cavity contained in a foam-discharging container of the present invention is 1.2 mass % or less. The content of the nonionic surfactant can be thus restricted, thereby effectively suppressing an increase in viscosity at a low temperature to result in an enhancement in storage stability. Examples of the nonionic surfactant include one or more selected from the group consisting of polyoxyethylene hardened castor oil, sucrose fatty acid ester, sorbitan fatty acid ester, glycerin fatty acid ester such as pentaglycerol monomyristate, alkyl glucoside, polyglycerol fatty acid ester, polyoxyethylene monoalkyl(or alkenyl)ether, a polyoxyethylene-polyoxypropylene copolymer, polyoxyethylene alkyl phenyl ether such as polyoxyethylene nonylphenyl ether, an amine oxide-based surfactant, mono-(or di-)ethanolamide, fatty acid alkanolamide such as coconut oil fatty acid diethanolamide, glycerin fatty acid ester such as monoglycerol stearate and decaglycerol monostearate, polyglycerol fatty acid ester such as decaglyceryl laurate, and polyglycol such as polyethylene polypropylene glycol. Among them, the nonionic surfactant to be used is preferably one or more selected from the group consisting of polyoxyethylene hardened castor oil, sucrose fatty acid ester, sorbitan fatty acid ester and polyglycerol fatty acid ester.

The content of the nonionic surfactant in the liquid composition for oral cavity contained in a foam-discharging container of the present invention is 1.2 mass % or less, preferably 1.1 mass % or less, more preferably 1.0 mass % or less, further preferably 0.7 mass % or less, further more preferably 0.5 mass % or less, or the liquid composition for oral cavity contained in a foam-discharging container of the present invention may not comprise the nonionic surfactant, in view of effectively suppressing an increase in viscosity at a low temperature, and enhancing adsorption of a specified bactericide such as isopropylmethylphenol and a specified anti-inflammatory agent in the oral cavity when the liquid composition for oral cavity contained in a foam-discharging container of the present invention comprises such a bactericide and agent as described below.

The content of the sugar alcohol which is a solid at 20° C., in the liquid composition for oral cavity contained in a foam-discharging container of the present invention, is 5 mass % or less. The sugar alcohol is a polyol other than the component (B), and the content of the sugar alcohol other than the component (B), which is a solid at 20° C., is preferably restricted in view of preventing unnecessary increase in pushing pressure upon discharging, in particular, the pushing pressure at the first pushing after storage, and improving the state at the first discharging after storage, for example, in view of effectively preventing clogging in the porous member of the foam-discharging container due to adhesion of the composition to the porous member and ensuring excellent dischargeability, even in a dry state or after storage at a high temperature. Examples of the sugar alcohol which is a solid at 20° C. include sorbitol, xylitol, erythritol, mannitol and reduced palatinose. The content of the sugar alcohol which is a solid at 20° C., in the liquid composition for oral cavity contained in a foam-discharging container of the present invention, is 5 mass % or less, preferably 3 mass % or less, more preferably 1 mass % or less, further preferably 0.5 mass % or less, further more preferably 0.1 mass % or less, particularly preferably 0.05 mass % or less, or preferably the sugar alcohol which is a solid at 20° C. is not contained, in view of retaining excellent dischargeability and enhancing uniform foaming performance.

The liquid composition for oral cavity contained in a foam-discharging container of the present invention may contain a thickening silica having an oil absorption of 180 to 350 mL/100 g, namely, a silica different from the abrasive silica and high in oil absorption. The content of the thickening silica in the liquid composition for oral cavity contained in a foam-discharging container of the present invention is preferably 1 mass % or less, more preferably 0.5 mass % or less, in view of ensuing good dischargeability from the container. The oil absorption is determined by the same measurement method as in the abrasive silica.

The liquid composition for oral cavity contained in a foam-discharging container of the present invention can further contain 0.005 mass % or more and 0.1 mass % or less of a cationic bactericide. The liquid composition for oral cavity contained in a foam-discharging container of the present invention retains a proper viscosity and also exhibits good low-temperature storage stability even after storage at a low temperature, while retaining good foam quality, and therefore enables embedding the cationic bactericide effectively in foam to effectively enhance adsorption onto the tooth surface and the oral mucosal surface (including the alveolar ridge surface) in the oral cavity, resulting in an enhancement in the bactericidal effect on bacteria causing tooth decay, periodontal disease, bad breath, and the like. Accordingly, even when the liquid composition for oral cavity contained in a foam-discharging container of the present invention contains, besides the cationic bactericide, triclosan or isopropylmethylphenol, i.e., a bactericide other than the cationic bactericide described below, it enables effective enhancement of adsorption of such a bactericide onto the tooth surface and the oral mucosal surface in the oral cavity, thereby exerting an excellent bactericidal effect. That is, the liquid composition for oral cavity contained in a foam-discharging container of the present invention is also useful as an absorption promoter in the oral cavity, for one or more bactericides selected from the group consisting of a cationic bactericide, triclosan and isopropylmethylphenol. The content of such triclosan or isopropylmethylphenol is as described below.

Examples of the cationic bactericide include one or more selected from the group consisting of a quaternary ammonium compound and a biguanide compound. Specific examples of the bactericide belonging to the quaternary ammonium compound include one or more selected from the group consisting of cetylpyridinium chloride, benzethonium chloride, dequalinium chloride, benzalkonium chloride, alkyl dimethyl ammonium chloride, alkyl trimethyl ammonium chloride and methylbenzethonium chloride. Specific examples of the bactericide belonging to the biguanide compound include one or more selected from the group consisting of chlorhexidine and a salt thereof. Among them, the cationic bactericide is preferably a quaternary ammonium compound, and preferably is one or two selected from the group consisting of cetylpyridinium chloride and benzethonium chloride, further preferably cetylpyridinium chloride, in view of enhancing adsorption to the oral mucosa for the liquid composition for oral cavity contained in a foam-discharging container of the present invention, which goes through a discharge port and is in the form of foam.

The content of the cationic bactericide in the liquid composition for oral cavity contained in a foam-discharging container of the present invention is preferably 0.005 mass % or more, more preferably 0.007 mass % or more, in view of effectively exhibiting bactericidal action. In addition, the content of the cationic bactericide in the liquid composition for oral cavity contained in a foam-discharging container of the present invention is preferably 0.1 mass % or less, more preferably 0.08 mass % or less, in view of ensuring good feeling of use. The content of the cationic bactericide in the liquid composition for oral cavity contained in a foam-discharging container of the present invention is then preferably 0.005 mass % or more and 0.1 mass % or less, more preferably from 0.007 to 0.08 mass %.

The liquid composition for oral cavity contained in a foam-discharging container of the present invention can further contain one or more selected from the group consisting of isopropylmethylphenol, triclosan, and glycyrrhizic acid or a salt thereof. Such isopropylmethylphenol and triclosan correspond to a bactericide other than the cationic bactericide, so-called a nonionic bactericide (non-cationic bactericide), and such glycyrrhizic acid and salt thereof correspond to an anti-inflammatory agent. The liquid composition for oral cavity contained in a foam-discharging container of the present invention, while retaining good foam quality, retains a proper viscosity and exhibits good low-temperature storage stability even after storage at a low temperature, and therefore the liquid composition for oral cavity enables embedding such a bactericide and anti-inflammatory agent effectively in foam to effectively enhance adsorption in the oral cavity. The salt of glycyrrhizic acid is preferably dipotassium glycyrrhizinate, and more preferably one or two selected from the group consisting of triclosan and dipotassium glycyrrhizinate in view of stability after low-temperature storage.

The content of one or more selected from the group consisting of isopropylmethylphenol, triclosan and glycyrrhizic acid or a salt thereof in the liquid composition for oral cavity contained in a foam-discharging container of the present invention is preferably 0.005 mass % or more, more preferably 0.007 mass % or more in view of effectively exerting the bactericidal action and the anti-inflammatory effect. In addition, the content of one or more selected from the group consisting of isopropylmethylphenol, triclosan and glycyrrhizic acid or a salt thereof in the liquid composition for oral cavity contained in a foam-discharging container of the present invention is preferably 0.1 mass % or less, more preferably 0.08 mass % or less in view of ensuring good feeling of use and flavor. The content of one or more selected from the group consisting of isopropylmethylphenol, triclosan and glycyrrhizic acid or a salt thereof in the liquid composition for oral cavity contained in a foam-discharging container of the present invention is preferably 0.005 mass % or more and 0.1 mass % or less, more preferably from 0.007 to 0.08 mass %. In addition, the content of isopropylmethylphenol in the liquid composition for oral cavity contained in a foam-discharging container of the present invention is preferably 0.02 mass % or less, more preferably 0.01 mass % or less in view of enhancing stability after low-temperature storage.

The liquid composition for oral cavity contained in a foam-discharging container of the present invention may also contain a polyol other than the sugar alcohol, which is a solid at 20° C., as the polyol other than the component (B). Examples of such a polyol which is a solid at 20° C. include sugars such as trehalose, maltose and isomalto; and polyethylene glycol having a mass average molecular weight of more than 1,000. The content of the polyol other than the sugar alcohol, which is a solid at 20° C., in the liquid composition for oral cavity contained in a foam-discharging container of the present invention is preferably 1 mass % or less, more preferably 0.5 mass % or less, further preferably 0.1 mass % or less, further more preferably 0.05 mass % or less, or the polyol other than the sugar alcohol, which is a solid at 20° C., may not be contained, in view of enhancing dischargeability.

The liquid composition for oral cavity contained in a foam-discharging container of the present invention can also contain an oily component (X) which is an oily component other than the component (A), the nonionic surfactant, isopropylmethylphenol, triclosan and glycyrrhizic acid. Examples of the oily component as the component (X) include one or more selected from the group consisting of a perfume; a preserving agent; a bactericide other than isopropylmethylphenol, triclosan and the cationic bactericide, and a medicinal agent other than glycyrrhizic acid.

Examples of the preserving agent include isobutyl parahydroxybenzoate, isopropyl parahydroxybenzoate, ethyl parahydroxybenzoate, butyl parahydroxybenzoate, propyl parahydroxybenzoate, methyl parahydroxybenzoate, benzoic acid, sodium benzoate, methyl salicylate, potassium sorbate, and sodium dehydroacetate.

The perfume may be any perfume exhibiting oil-solubility, and examples thereof include natural perfume components such as peppermint oil, spearmint oil, cinnamon oil, anise oil, eucalyptus oil, wintergreen oil, quassia oil, clove oil, thyme oil, sage oil, sage clary oil, nutmeg oil, funnel oil, lemon oil, orange oil, mint oil, cardamom oil, coriander oil, basil oil, mandarin oil, lime oil, lavender oil, rosemary oil, ginger oil, grapefruit oil, laurel oil, chamomile oil, caraway oil, marjoram oil, bay oil, lemongrass oil, lemon balm oil, pimento berry oil, palmarosa oil, olibanum oil, pine needle oil, petitgrain oil, neroli oil, rose oil and jasmine oil, and perfume components obtained by processing treatment of such natural perfume components; single perfume components such as menthol, pulegol, carvone, anethole, cineol, methyl salicylate, cinnamic aldehyde, eugenol, 3-1-menthoxypropane-1,2-diol, thymol, citronellyl acetate, linalool, linalyl acetate, geraniol, geranyl acetate, citronellol, limonene, menthone, menthyl acetate, N-substituted-p-menthane-3-carboxamide, pinene, octyl aldehyde, citral, pulegone, carbyl acetate, dihydrocarbyl acetate, anisaldehyde, benzaldehyde, camphor, lactone, ethyl acetate, ethyl butyrate, allyl cyclohexyl propionate, methyl anthranilate, ethyl methyl phenyl glycidate, vanillin, undecalactone, hexanal, butyl acetate, isoamyl acetate, hexenol, dimethyl sulfide, cyclotene, furfural, trimethylpyrazine, ethyl lactate, methyl lactate and ethyl thioacetate; and formulated perfume components such as strawberry flavor, apple flavor, banana flavor, pineapple flavor, grape flavor, mango flavor, butter flavor, milk flavor, fruit mix flavor and tropical fruit flavor.

Examples of the medicinal agent include anti-inflammatory agents such as azulenes, tocopherols, hinokitiol, glycyrrhetinic acid and dihydrocholesterol; and vegetable extract oil such as chamomile oil and ratanhia oil. Examples of the azulenes include azulene, guaiazulene and guaiazulene sulfonic acid, examples of the tocopherols include dl-α-tocopherol acetate and tocopherol nicotinate, and examples of the glycyrrhetinic acid include α-glycyrrhetinic acid and β-glycyrrhetinic acid.

When the liquid composition for oral cavity contained in a foam-discharging container of the present invention contains the oily component as the component (X), the mass ratio of the component (X) to the total content of the component (A) and the nonionic surfactant, $((X)/((A)+\text{nonionic surfactant}))$ is preferably 0.05 or more, more preferably 0.08 or more, further preferably 0.1 or more, in view of ensuring good feeling of use in the oral cavity, and enhancing adsorption of one or more selected from the group consisting of isopropylmethylphenol, triclosan and glycyrrhizic acid or a salt thereof in the oral cavity when the liquid composition for oral cavity contained in a foam-discharging container of the present invention contains these compounds therein. In addition, the mass ratio of the component (X) to the total content of the component (A) and the nonionic surfactant, $(X)/((A)+\text{nonionic surfactant})$, is preferably 5 or less, more preferably 4.5 or less, further preferably 4 or less in view of ensuring storage stability at a low temperature. The mass ratio of the component (X) to the total content of the component (A) and the nonionic surfactant, $(X)/((A)+\text{nonionic surfactant})$, is then preferably from 0.05 to 5, more preferably from 0.08 to 4.5, further preferably from 0.1 to 4.

The content of the oily component as the component (X) in the liquid composition for oral cavity contained in a foam-discharging container of the present invention is preferably 0.1 mass % or more, more preferably 0.15 mass % or more, further preferably 0.2 mass % or more, and preferably 2 mass % or less, more preferably 1.8 mass % or less, further preferably 1.5 mass % or less in view of ensuring preservation stability at a low temperature while achieving good flavor, feeling of use, and the like.

The liquid composition for oral cavity contained in a foam-discharging container of the present invention can appropriately contain, in addition to the above components, a pH adjuster, a pigment, a dye, and the like as long as the effect of the present invention is not impaired.

The liquid composition for oral cavity contained in a foam-discharging container of the present invention is filled into a foam-discharging container provided with a discharge port. When the liquid composition for oral cavity contained in a foam-discharging container of the present invention is used, the liquid composition for oral cavity as the content is directly discharged into the oral cavity through the discharge port with which the foam-discharging container is provided, and the liquid composition for oral cavity going through the discharge port is applied into the oral cavity in the form of foam. Thus, the liquid composition for oral cavity can be spread into the oral cavity thoroughly, while good foam quality is provided to thereby afford excellent feeling of use, and therefore the composition is also high in usability as a foam liquid composition for oral cavity. Furthermore, even when the liquid composition for oral cavity contained in a foam-discharging container of the present invention contains the one or more selected from the group consisting of isopropylmethylphenol, triclosan and glycyrrhizic acid or a salt thereof, or even when the composition contains one or more bactericides selected from the group consisting of the cationic bactericide, triclosan and isopropylmethylphenol, the composition, while enhancing adsorption of such components in the oral cavity to exert desired effects, can favorably maintain such performances even after low-temperature storage, as a foam liquid composition for oral cavity.

As the foam-discharging container into which the liquid composition for oral cavity is filled, any container may be adopted as long as it is provided with a discharge port, and may be a non-aerosol type container or an aerosol type container.

The non-aerosol type container is also referred to as a "non-aerosol container", and is a normal pressure container not requiring for a propellant such as a compressed gas, and examples of such a container include a squeeze type container and a pump type container. Such a container is preferably a container including a porous member provided with a mesh or a plurality of pores interposed in the flow path of the content located from the container main body towards the discharge port, in view of favorably forming the content into a foam composition when going through the discharge port, and providing good retainability and homogeneity of the foam formed to result in an enhancement in feeling of use, and the like.

The squeeze type container is also referred to as a "squeeze container", and by squeezing and deforming a trunk of a deformable container main body, the content is mixed with air pressure-fed from the inside of a head space, while, if necessary, allowing the mixture to go through a porous member, to form and discharge foam from the discharge port. Specifically, for example, any container described in JP-A-07-215352, JP-U-58-174272 and JP-U-62-42787 can be used.

The pump type container is also referred to as a "pump container", and by pressing a pump head provided in a foam discharger having a discharge port, the content is mixed with air flowing-in from the outside, while, if necessary, allowing the mixture to go through a porous member, to form and discharge foam from the discharge port. The container is usually provided with an air cylinder for allowing air to flow in from the outside and a liquid cylinder serving as the flow path of the content, as well as a mixing chamber for mixing the content with air pressure-fed by pressing of the pump head. Specifically, for example, any container described in JP-A-07-315463, JP-A-08-230961 and JP-U-03-7963 can be used.

The aerosol type container is also referred to as an "aerosol container", and is a container filled with a compressed gas as a propellant. When the content is discharged from the discharge port, foam is formed with gas taken in via a valve mechanism. The compressed gas used is preferably a gas containing 90 mass % or more of carbon dioxide gas.

The foam-discharging container for use in the present invention is preferably a squeeze container, more preferably a container provided with any of #90 to #305 meshes in the flow path of the content located from the main body of the container towards the discharge port, in view of usability, namely, in view of directly easily discharging the content from the discharge port into the oral cavity, and also excellent convenience and portability.

The viscosity of the liquid composition for oral cavity contained in a foam-discharging container of the present invention is preferably 85 mPa·s or less, more preferably 65 mPa·s or less, further preferably 60 mPa·s or less, furthermore preferably 55 mPa·s or less, particularly preferably 50 mPa·s or less, and preferably 5 mPa·s or more, more preferably 10 mPa·s or more at both 25° C. and −5° C. in view of improving dischargeability at a low temperature. Herein, the viscosity of the liquid composition for oral cavity of the present invention is obtained by measuring the liquid viscosity (mPa·s) at 25° C. or −5° C. by use of a BL viscometer (manufactured by Toki Sangyo Co., Ltd., M1 rotor, rotation speed: 30 rpm/min).

With respect to the above embodiments of the present invention, the liquid composition for oral cavity contained in a foam-discharging container, and the method of using the same are further disclosed.

[1] A liquid composition for oral cavity contained in a foam-discharging container, comprising the following components (A), (B) and (C):

(A) 0.3 mass % or more and 2.5 mass % or less in total of one or more surfactants selected from the group consisting of an anionic surfactant (a-1) selected from the group consisting of an N-acylamino acid salt, an alkyl sulfate ester salt, an alkyl phosphate salt and an α-olefin sulfonate salt, and an amphoteric surfactant (a-2);

(B) 10 mass % or more and 40 mass % or less in total of one or more polyols selected from the group consisting of glycerin, propylene glycol, butylene glycol, and polyethylene glycol having an average molecular weight of 1,000 or less; and (C) 50 mass % or more and 89 mass % or less of water; wherein a content of the component (a-1) is 1.2 mass % or less, or the component (a-1) is not comprised, and a content of the component (a-2) is 0.25 mass % or more and 1.5 mass % or less and furthermore, a content of ethanol is 3 mass % or less, a content of an abrasive powder is 0.5 mass % or less, a content of a binder is 0.3 mass % or less, a content of a nonionic surfactant is 1.2 mass % or less, and the content of a sugar alcohol which is a solid at 20° C. is 5 mass % or less.

[2] The liquid composition for oral cavity contained in a foam-discharging container according to [1], wherein the component (a-1) is preferably one or more selected from the group consisting of an N-lauroylsarcosine salt, an N-lauroyl methyl taurine salt, an N-lauroyl taurine salt, an N-myristoylglutamic acid salt, an N-lauroylglutamic acid salt, a lauryl sulfate salt, a lauryl phosphate salt and an α-olefin (C14 to 16) sulfonate salt, more preferably one or more selected from the group consisting of an N-lauroyl methyl taurine salt, an N-myristoyl-L-glutamic acid salt and a lauryl sulfate salt, and the salt is preferably an alkali metal salt, more preferably a sodium salt or a potassium salt, further preferably a sodium salt.

[3] The liquid composition for oral cavity contained in a foam-discharging container according to [1] or [2], wherein a content of the component (a-1) is 1.2 mass % or less, preferably 1 mass % or less, more preferably 0.8 mass % or less, and preferably 0.1 mass % or more, more preferably 0.2 mass % or more; or the component (a-1) is not comprised.

[4] The liquid composition for oral cavity contained in a foam-discharging container according to any one of [1] to [3], wherein a content of an anionic surfactant being a fatty acid or a salt thereof is preferably 0.2 mass % or less, more preferably 0.1 mass % or less, further preferably 0.01 mass % or less, and preferably more than 0 mass %; or further preferably the anionic surfactant being a fatty acid or a salt thereof is not contained.

[5] The liquid composition for oral cavity contained in a foam-discharging container according to any one of [1] to [4], wherein the component (a-2) is preferably one or more selected from the group consisting of coconut oil fatty acid amide alkyl betaine and alkyl sulfobetaine, more preferably coconut oil fatty acid amide alkyl betaine, further preferably coconut oil fatty acid amide propyl betaine.

[6] The liquid composition for oral cavity contained in a foam-discharging container according to any one of [1] to [5], wherein the total content of the one or more surfactants selected from the group consisting of the component (a-1) and the component (a-2), as the component (A), is preferably 0.4 mass % or more, more preferably 0.5 mass % or more, further preferably 0.6 mass % or more, and preferably 2.2 mass % or less, more preferably 2 mass % or less, further preferably 1.7 mass % or less, further more preferably 1.3 mass % or less.

[7] The liquid composition for oral cavity contained in a foam-discharging container according to any one of [1] to [6], wherein a mass ratio of the component (a-2) to the component (a-1), (a-2)/(a-1), is preferably 0.5 or more, more preferably 0.55 or more, further preferably 0.6 or more, further more preferably 0.65 or more, and preferably 3 or less, more preferably 2.5 or less, further preferably 2 or less, further more preferably 1.8 or less, further more preferably 1.3 or less.

[8] The liquid composition for oral cavity contained in a foam-discharging container according to any one of [1] to [7], wherein the component (B) is preferably one or more polyols selected from the group consisting of glycerin, propylene glycol and butylene glycol.

[9] The liquid composition for oral cavity contained in a foam-discharging container according to any one of [1] to [8], wherein the total content of the component (B) is preferably 12 mass % or more, more preferably 15 mass % or more, and preferably 37 mass % or less, more preferably 35 mass % or less, further preferably 32 mass % or less, a content of the polyethylene glycol having an average molecular weight of 1,000 or less used as the component (B) is preferably 7 mass % or less, more preferably 5 mass % or less, further preferably 3 mass % or less, further more preferably 2 mass % or less, or preferably the poly(ethylene glycol) having an average molecular weight of 1,000 or less is not contained.

[10] The liquid composition for oral cavity contained in a foam-discharging container according to any one of [1] to [9], wherein a content of a polyol other than the sugar alcohol which is a solid at 20° C. is preferably 1 mass % or less, more preferably 0.5 mass % or less, further preferably 0.1 mass % or less, further more preferably 0.05 mass % or less; or the polyol which is a solid at 20° C. is not contained.

[11] The liquid composition for oral cavity contained in a foam-discharging container according to any one of [1] to [10], wherein the mass ratio of the component (B) to the component (A), (B)/(A), is preferably 6 or more, more preferably 8 or more, further preferably 10 or more, further more preferably 12 or more, and preferably 130 or less, more preferably 90 or less, further preferably 70 or less, further more preferably 55 or less, further more preferably 52 or less.

[12] The liquid composition for oral cavity contained in a foam-discharging container according to any one of [1] to [11], wherein a content of the component (C) is preferably 55 mass % or more, more preferably 60 mass % or more, further preferably 65 mass % or more, and preferably 86 mass % or less, more preferably 83 mass % or less.

[13] The liquid composition for oral cavity contained in a foam-discharging container according to any one of [1] to [12], wherein a mass ratio of the component (A) to the component (C), (A)/(C), is preferably $0.5 \times 10^{-2}$ or more, more preferably $0.6 \times 10^{-2}$ or more, further preferably $0.75 \times 10^{-2}$ or more, further more preferably $0.8 \times 10^{-2}$ or more, and preferably $5 \times 10^{-2}$ or less, more preferably $4.4 \times 10^{-2}$ or less, further preferably $2.5 \times 10^{-2}$ or less, further more preferably $2 \times 10^{-2}$ or less.

[14] The liquid composition for oral cavity contained in a foam-discharging container according to any one of [1] to [13], wherein the content of ethanol is preferably 2.5 mass % or less, more preferably 2 mass % or less, further preferably 1 mass % or less, and preferably more than 0 mass %, or ethanol is not contained.

[15] The liquid composition for oral cavity contained in a foam-discharging container according to any one of [1] to [14], wherein the content of the abrasive powder is preferably 0.4 mass % or less, more preferably 0.3 mass % or less, and preferably more than 0 mass %, or the abrasive powder is not contained.

[16] The liquid composition for oral cavity contained in a foam-discharging container according to any one of [1] to [15], wherein the content of the binder is preferably 0.28 mass % or less, more preferably 0.25 mass % or less, and preferably 0.05 mass % or more, more preferably 0.1 mass % or more, or the binder is not contained.

[17] The liquid composition for oral cavity contained in a foam-discharging container according to any one of [1] to [16], wherein the content of the nonionic surfactant is preferably 1.1 mass % or less, more preferably 1.0 mass % or less, further preferably 0.7 mass % or less, further more preferably 0.5 mass % or less, or the nonionic surfactant is not contained.

[18] The liquid composition for oral cavity contained in a foam-discharging container according to any one of [1] to [17], wherein the content of the sugar alcohol which is a solid at 20° C. is preferably 3 mass % or less, more preferably 1 mass % or less, further preferably 0.5 mass % or less, further more preferably 0.1 mass % or less, further more preferably 0.05 mass % or less, or the sugar alcohol which is a solid at 20° C. is not contained.

[19] The liquid composition for oral cavity contained in a foam-discharging container according to any one of [1] to [18], wherein the sugar alcohol which is a solid at 20° C. is one or more selected from the group consisting of sorbitol, xylitol, erythritol, mannitol and reduced palatinose.

[20] The liquid composition for oral cavity contained in a foam-discharging container according to any one of [1] to [19], further comprising a cationic bactericide, wherein the cationic bactericide is preferably one or more selected from the group consisting of a quaternary ammonium compound and a biguanide compound.

[21] The liquid composition for oral cavity contained in a foam-discharging container according to [20], wherein the content of the cationic bactericide is preferably 0.005 mass % or more, more preferably 0.007 mass % or more, and preferably 0.1 mass % or less, more preferably 0.08 mass % or less.

[22] The liquid composition for oral cavity contained in a foam-discharging container according to any one of [1] to [21], further comprising one or more selected from the group consisting of isopropylmethylphenol, triclosan and glycyrrhizic acid or a salt thereof, wherein the content thereof is preferably 0.005 mass % or more, more preferably 0.007 mass % or more, and preferably 0.1 mass % or less, more preferably 0.08 mass % or less.

[23] The liquid composition for oral cavity contained in a foam-discharging container according to any one of [1] to [19], further comprising one or more bactericides selected from the group consisting of a cationic bactericide, triclosan and isopropylmethylphenol.

[24] The liquid composition for oral cavity contained in a foam-discharging container according to [22] or [23], wherein a content of isopropylmethylphenol is preferably 0.02 mass % or less, more preferably 0.01 mass % or less.

[25] The liquid composition for oral cavity contained in a foam-discharging container according to any one of [1] to [24], comprising an oily component (X) which is an oily component other than the component (A), the nonionic surfactant, isopropylmethylphenol, triclosan and glycyrrhizic acid, wherein the mass ratio of the component (X) to the total content of the component (A) and the nonionic surfactant, (X)/((A)+nonionic surfactant), is preferably 0.05 or more, more preferably 0.08 or more, further preferably 0.1 or more, and preferably 5 or less, more preferably 4.5 or less, further preferably 4 or less.

[26] The liquid composition for oral cavity contained in a foam-discharging container according to [25], wherein the oily component (X) is one or more selected from the group consisting of a perfume, a preserving agent and a medicinal agent.

[27] The liquid composition for oral cavity contained in a foam-discharging container according to [25] or [26], wherein a content of the oily component (X) is preferably 0.1 mass % or more, more preferably 0.15 mass % or more, further preferably 0.2 mass % or more, and preferably 2 mass % or less, more preferably 1.8 mass % or less, further preferably 1.5 mass % or less.

[28] The liquid composition for oral cavity contained in a foam-discharging container according to any one of [1] to [27], wherein the foam-discharging container is preferably a non-aerosol container or an aerosol container provided with a discharge port, preferably a non-aerosol container selected from the group consisting of a squeeze container and a pump container.

[29] Use of the liquid composition for oral cavity contained in a foam-discharging container according to any one of [1] to [28], for direct application from a container into the oral cavity in a form of foam.

[30] Use of the liquid composition for oral cavity contained in a foam-discharging container according to any one of [20] to [28], for enhancing adsorption in the oral cavity, of one or more selected from the group consisting of isopropylmethylphenol, triclosan and glycyrrhizic acid or a salt thereof, or one or more bactericides selected from the group consisting of a cationic bactericide, triclosan and isopropylmethylphenol.

[31] A method of using the liquid composition for oral cavity contained in a foam-discharging container according to any one of [1] to [28], comprising directly discharging the liquid composition for oral cavity contained in a foam-discharging container, into the oral cavity through a discharge port provided in the foam-discharging container, to apply the liquid composition for oral cavity contained in a foam-discharging container, which has gone through the discharge port, in the form of foam into the oral cavity.

[32] A foam liquid composition comprising the following components (A), (B) and (C):

(A) 0.3 mass % or more and 2.5 mass % or less in total of one or more surfactants selected from the group consisting of an anionic surfactant (a-1) selected from the group consisting of an N-acylamino acid salt, an alkyl sulfate ester salt, an alkyl phosphate salt and an α-olefin sulfonate salt, and an amphoteric surfactant (a-2);

(B) 10 mass % or more and 40 mass % or less in total of one or more polyols selected from the group consisting of glycerin, propylene glycol, butylene glycol, and polyethylene glycol having an average molecular weight of 1,000 or less; and (C) 50 mass % or more and 89 mass % or less of water; wherein a content of the component (a-1) is 1.2 mass % or less, or the component (a-1) is not comprised, and a content of the component (a-2) is 0.25 mass % or more and 1.5 mass % or less, and furthermore, a content of ethanol is 3 mass % or less, a content of an abrasive powder is 0.5 mass % or less, a content of a binder is 0.3 mass % or less, a content of a nonionic surfactant is 1.2 mass % or less, and a content of a sugar alcohol which is a solid at 20° C. is 5 mass % or less.

[33] The foam liquid composition for oral cavity according to [32], which is an agent for promoting absorption, in the oral cavity, of one or more bactericide selected from the group consisting of a cationic bactericide, triclosan and isopropylmethylphenol.

EXAMPLES

Hereinafter, the present invention will be specifically described based on Examples. Unless particularly indicated in Tables, the content of each component is represented by "mass %".

Examples 1 to 36 and Comparative Examples 1 to 9

Each liquid composition for oral cavity was prepared according to each formulation shown in Tables 1 to 6, and subjected to each of measurements and evaluations according to the following methods.

The results are shown in Tables 1 to 6.

(Measurement of Liquid Viscosity after Low-temperature Storage (−5° C.))

Each of the resulting liquid compositions for oral cavity was filled into a glass bottle, stored at −5° C. for 3 days, and thereafter subjected to measurement of the liquid viscosity (mPa·s), with being kept at −5° C., by use of a BL viscometer (manufactured by Toki Sangyo Co., Ltd., M1 rotor, rotation speed: 30 rpm/min).

(Measurement of Foam Viscosity)

One hundred grams of each of the resulting liquid compositions for oral cavity was filled into a pump foamer container (manufactured by Daiwa Can Company, F5 pump foamer, two meshes, mesh size: #255/#255), the content was discharged from the discharge port, and the foam viscosity (mPa·s) was measured by use of a BH viscometer (manufactured by Toki Sangyo Co., Ltd., H2 rotor, rotation speed: 5 rpm/min) at room temperature (25° C.)

(Evaluation of Low-temperature Stability)

Each of the resulting liquid compositions for oral cavity was filled into a glass bottle and stored at −5° C. for 3 days, and thereafter the liquid composition for oral cavity as the content was visually observed from the outside of the glass bottle and evaluated according to the following criteria.

A: fully transparent and uniform
a: generally transparent and uniform
B: slightly clouded, but uniform
C: clouded, but no precipitate confirmed
D: some precipitate confirmed (Foam Quality Upon Discharging)

One hundred grams of each of the resulting o liquid compositions for oral cavity was filled into the pump foamer container, and the foam quality upon discharging of the content from the discharge port was visually evaluated according to the following criteria.

A: foaming was good, and fineness of the foam was high and uniform
B: foaming was good, but fineness of the foam was ununiform
C: the pump was hardly pushed, and therefore the content could not be sufficiently discharged
D: pushing property of the pump was good, but foaming was poor to result in coarse foam (The State of Discharge Port after High-Temperature Storage)

One hundred grams of each of the resulting liquid compositions for oral cavity was filled into the pump foamer container, the content was discharged through the discharge port and subsequently stored at 40° C. for 14 days, and thereafter the porous member (mesh) of the pump foamer was taken out, and visually observed and evaluated according to the following criteria.

(The State of Discharge Port after High-Temperature Storage)

A: no adhered substance was found on the mesh
B: some adhered substance was found on the mesh
C: some solid adhered substance was found on the mesh (Adsorption Amount of Foam or Liquid Medicinal Component)

Adsorption, in the oral cavity, of the medicinal component (cetylpyridinium chloride, benzethonium chloride, triclosan, and dipotassium glycyrrhizinate), was evaluated according to the following method. Here, each of the resulting liquid compositions for oral cavity discharged from the discharge port of the pump foamer container was adopted as the foam, and each of the resulting liquid compositions for oral cavity as such was adopted as the liquid.

First, a cylindrical container (inner diameter: 2.5 cm) having no bottom surface and an open upper surface was disposed on each silicone sheet, and the lower end of the side surface of the container was closely contacted with the silicone sheet. Next, 1.5 g of the foam or the liquid was loaded into each container from the upper surface of the container, and the foam or the liquid was applied onto the surface of the silicone sheet surrounded by the side surface of the container and bared. Next, the tip of a pipette was inserted from the upper surface of the container, and pipetting was performed for 30 seconds.

The resulting silicone sheet was washed with 2 mL of purified water three times, 2 mL of an extraction liquid (mobile phase corresponding to each medicinal component, shown below) was applied thereto for 30 seconds and then collected, and thereafter the amount of each medicinal component ($ng/cm^2$) was quantitatively determined by high-performance liquid chromatography (HPLC) according to the following measurement conditions.

<HPLC Measurement Conditions>

Apparatus: high-performance liquid chromatogram La chromElite

Quantitative Determination of Amounts of Cetylpyridinium Chloride and Benzethonium Chloride Detector: ultraviolet absorptiometer (measurement wavelength: CPC=260 nm, BTC=215 nm)

Column: CAPCELL PAK SCX UG80 (4.6×100 mm, 5 μm) (Shiseido Japan Co., Ltd.)

Column temperature: 40° C.

Mobile phase: mixed liquid of methanol/water (3:1)+0.05 mol/L sodium perchlorate-hydrate Flow rate: 1.2 mL/min Quantitative Determination of Amount of Triclosan Detector: ultraviolet absorptiometer (measurement wavelength: 280 nm)

Column: L-column ODS (4.6×100 mm, 5 μm) (Chemicals Evaluation and Research Institute, Japan)

Column temperature: 40° C.

Mobile phase: mixed liquid of methanol/water (4:1)+0.1 w/v % phosphoric acid

Flow rate: 1.0 mL/min

Quantitative Determination of Amount of Dipotassium Glycyrrhizinate

Detector: ultraviolet absorptiometer (measurement wavelength: 254 nm)

Column: L-column ODS (4.6×100 mm, 5 μm) (Chemicals Evaluation and Research Institute, Japan)

Column temperature: 40° C.

Mobile phase: mixed liquid of methanol/water (65:35)+ 0.1 w/v % phosphoric acid

Flow rate: 1.0 mL/min

TABLE 1

|  |  | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|
| (a-1) | Sodium lauryl sulfate | 0.5 | 0.5 | 0.5 | 0.5 | 0.5 | 0.5 | 0.5 | 0.75 | 0.75 |
|  | Sodium lauroyl methyl taurine*[1] |  |  |  |  |  |  |  |  |  |
|  | Sodium N-myristoyl-L-glutamate*[2] |  |  |  |  |  |  |  |  |  |
| (a-2) | Coconut oil fatty acid amide propyl betaine*[3] | 0.5 | 0.5 | 0.5 | 0.5 | 0.5 | 0.5 | 1 | 0.5 | 0.75 |
|  | 2-Alkyl-N-carboxymethyl-N-hydroxyethyl imidazolinium betaine*[4] |  |  |  |  |  |  |  |  |  |
| (B) | Glycerin | 20 | 20 | 10 | 10 |  | 20 | 20 | 20 | 20 |
|  | Propylene glycol | 10 | 10 | 10 |  | 10 | 10 | 10 | 10 | 10 |
| Binder | (ι-) Carrageenan*[5] | 0.1 | 0.1 | 0.1 | 0.1 | 0.1 | 0.1 | 0.1 | 0.1 | 0.1 |
|  | Sodium carboxymethylcellulose*[6] | 0.05 | 0.05 | 0.05 | 0.05 | 0.05 | 0.05 | 0.05 | 0.05 | 0.05 |
|  | Cetylpyridinium chloride | 0.01 |  | 0.01 | 0.01 | 0.01 | 0.01 | 0.01 | 0.01 | 0.01 |
|  | Benzethonium chloride |  | 0.01 |  |  |  |  |  |  |  |

TABLE 1-continued

|   |   | | | | | | | | | |
|---|---|---|---|---|---|---|---|---|---|---|
| (X) | Perfume | 0.2 | 0.2 | 0.2 | 0.2 | 0.2 | 0.2 | 0.2 | 0.2 | 0.2 |
|   | Saccharine sodium | 0.03 | 0.03 | 0.03 | 0.03 | 0.03 | 0.03 | 0.03 | 0.03 | 0.03 |
|   | Sodium pyrophosphate | | | | | | | | | |
|   | Ethanol | | | | | | 3 | | | |
| (C) | Water | 68.61 | 68.61 | 78.61 | 88.61 | 88.61 | 65.61 | 68.11 | 68.36 | 68.11 |
| Total | | 100 | 100 | 100 | 100 | 100 | 100 | 100 | 100 | 100 |
|   | (a-2)/(a-1) | 1 | 1 | 1 | 1 | 1 | 1 | 2 | 0.67 | 1 |
|   | Ethanol/(a-1) | — | — | — | — | — | 6 | — | — | — |
|   | Total of binder | 0.15 | 0.15 | 0.15 | 0.15 | 0.15 | 0.15 | 0.15 | 0.15 | 0.15 |
|   | Total of component (B) | 30 | 30 | 20 | 10 | 10 | 30 | 30 | 30 | 30 |
|   | Total of component (A) ((a-1) + (a-2)) | 1 | 1 | 1 | 1 | 1 | 1 | 1.5 | 1.25 | 1.5 |
|   | (X)/((A) + Nonionic surfactant) | 0.20 | 0.20 | 0.20 | 0.20 | 0.20 | 0.20 | 0.13 | 0.16 | 0.13 |
|   | (A)/(C)(×10$^{-2}$) | 1.46 | 1.46 | 1.27 | 1.13 | 1.13 | 1.52 | 2.20 | 1.83 | 2.20 |
| Liquid viscosity after low-temperature storage (−5° C.) (mPa · s) | | 32 | 37 | 30 | 15 | 17 | 43 | 63 | 33 | 46 |
| Foam viscosity upon discharging from container (mPa · s) | | 6093 | 5896 | 5499 | 4324 | 4311 | 6884 | 6493 | 6507 | 5898 |
| Low-temperature stability (−5° C.) | | A | A | A | A | A | A | A | A | A |

|   |   | Ex. 10 | Ex. 11 | Ex. 12 | Ex. 13 | Ex. 14 | Ex. 15 | Ex. 16 | Ex. 17 |
|---|---|---|---|---|---|---|---|---|---|
| (a-1) | Sodium lauryl sulfate | 0.5 | | 0.3 | | 0.5 | 0.5 | 0.5 | 0.5 |
|   | Sodium lauroyl methyl taurine*[1] | | | | 0.5 | | | | |
|   | Sodium N-myristoyl-L-glutamate*[2] | | | | | | 0.1 | | |
| (a-2) | Coconut oil fatty acid amide propyl betaine*[3] | 0.75 | 1 | 0.3 | 0.5 | 0.5 | | 0.5 | 0.5 |
|   | 2-Alkyl-N-carboxymethyl-N-hydroxyethyl imidazolinium betaine*[4] | | | | | | 0.5 | | |
| (B) | Glycerin | 20 | 20 | 20 | 20 | 20 | 20 | 20 | 20 |
|   | Propylene glycol | 10 | 10 | 10 | 10 | 10 | 10 | 10 | 10 |
| Binder | (ι-) Carrageenan*[5] | 0.1 | 0.1 | 0.1 | 0.1 | 0.1 | 0.1 | 0.05 | 0.1 |
|   | Sodium carboxymethylcellulose*[6] | 0.05 | 0.05 | 0.05 | 0.05 | 0.05 | 0.05 | 0.05 | 0.02 |
|   | Cetylpyridinium chloride | 0.01 | 0.01 | 0.01 | 0.01 | 0.01 | 0.01 | 0.01 | 0.01 |
|   | Benzethonium chloride | | | | | | | | |
| (X) | Perfume | 0.2 | 0.2 | 0.2 | 0.2 | 0.5 | 0.2 | 0.2 | 0.2 |
|   | Saccharine sodium | 0.03 | 0.03 | 0.03 | 0.03 | 0.03 | 0.03 | 0.03 | 0.03 |
|   | Sodium pyrophosphate | | | | | 0.05 | | | |
|   | Ethanol | | | | | | | | |
| (C) | Water | 68.36 | 68.61 | 69.01 | 68.61 | 68.16 | 68.61 | 68.66 | 68.64 |
| Total | | 100 | 100 | 100 | 100 | 100 | 100 | 100 | 100 |
|   | (a-2)/(a-1) | 1.50 | — | 1 | 1 | 0.83 | 1 | 1 | 1 |
|   | Ethanol/(a-1) | — | — | — | — | — | — | — | — |
|   | Total of binder | 0.15 | 0.15 | 0.15 | 0.15 | 0.15 | 0.15 | 0.1 | 0.12 |
|   | Total of component (B) | 30 | 30 | 30 | 30 | 30 | 30 | 30 | 30 |
|   | Total of component (A) ((a-1) + (a-2)) | 1.25 | 1 | 0.6 | 1 | 1.1 | 1 | 1 | 1 |
|   | (X)/((A) + Nonionic surfactant) | 0.16 | 0.20 | 0.33 | 0.20 | 0.45 | 0.20 | 0.20 | 0.20 |
|   | (A)/(C)(×10$^{-2}$) | 1.83 | 1.46 | 0.87 | 1.46 | 1.61 | 1.46 | 1.46 | 1.46 |
| Liquid viscosity after low-temperature storage (−5° C.) (mPa · s) | | 47 | 22 | 23 | 30 | 33 | 56 | 19 | 24 |
| Foam viscosity upon discharging from container (mPa · s) | | 6256 | 7257 | 5489 | 6454 | 5722 | 7442 | 6228 | 6073 |
| Low-temperature stability (−5° C.) | | A | A | A | A | A | A | A | A |

*[1]Nikkol LMT, Nikko Chemicals Co., Ltd.
*[2]Amisoft MS11, Ajinomoto Co., Inc.
*[3]Amphitol 55AB, Kao Corporation, cocamidopropyl betaine
*[4]Amphitol 20YB, Kao Corporation, sodium cocoamphoacetate
*[5]Soageena VX23, Mitsubishi-Kagaku Foods Corporation
*[6]Sunrose F35SH, Nippon Paper Industries Co., Ltd.

TABLE 2

|   |   | Ex. 18 | Ex. 19 | Ex. 20 | Ex. 21 | Ex. 22 | Ex. 23 | Ex. 24 | Ex. 25 | Ex. 26 |
|---|---|---|---|---|---|---|---|---|---|---|
| (a-1) | Sodium lauryl sulfate | 0.5 | 0.5 | 0.5 | 0.5 | 0.5 | 0.5 | 0.5 | 0.5 | 0.5 |
| (a-2) | Coconut oil fatty acid amide propyl betaine*[3] | 0.5 | 0.5 | 0.5 | 0.5 | 0.5 | 0.5 | 0.5 | 0.5 | 0.5 |
| (B) | Glycerin | 20 | 20 | 20 | 20 | 20 | 20 | | 20 | |
|   | Propylene glycol | 10 | 10 | 10 | 10 | 10 | 10 | 10 | 10 | 10 |
| Binder | (ι-) Carrageenan*[5] | 0.1 | | | | 0.1 | 0.1 | 0.1 | 0.1 | |
|   | Sodium carboxymethylcellulose*[6] | | 0.1 | | | 0.05 | 0.05 | 0.05 | 0.05 | |
|   | Hydroxyethylcellulose*[7] | | | 0.1 | | | | | | |
| Nonionic surfactant | Polyoxyethylene hardened castor oil (E.O. 40) | | | | | | 0.5 | | 1 | |
|   | Cetylpyridinium chloride | 0.01 | 0.01 | 0.01 | 0.01 | 0.01 | 0.05 | 0.01 | 0.01 | 0.01 |

TABLE 2-continued

| | | | | | | | | | | |
|---|---|---|---|---|---|---|---|---|---|---|
| (X) | Perfume | 0.2 | 0.2 | 0.2 | 0.2 | 0.2 | 0.2 | 0.2 | 0.6 | 0.2 |
| | Saccharine sodium | 0.03 | 0.03 | 0.03 | 0.03 | 0.03 | 0.03 | 0.03 | 0.03 | 0.03 |
| | Ethanol | | | | | | | | | |
| (C) | Water | 68.66 | 68.66 | 68.66 | 68.76 | 68.11 | 68.57 | 88.61 | 67.21 | 88.76 |
| Total | | 100 | 100 | 100 | 100 | 100 | 100 | 100 | 100 | 100 |
| | (a-2)/(a-1) | 1 | 1 | 1 | 1 | 1 | 1 | 1 | 1 | 1 |
| | Ethanol/(a-1) | — | — | — | — | — | — | — | — | — |
| | Total of binder | 0.1 | 0.1 | 0.1 | 0 | 0.15 | 0.15 | 0.15 | 0.15 | 0 |
| | Total of component (B) | 30 | 30 | 30 | 30 | 30 | 30 | 10 | 30 | 10 |
| | Total of component (A) ((a-1) + (a-2)) | 1 | 1 | 1 | 1 | 1 | 1 | 1 | 1 | 1 |
| | (X)/((A) + Nonionic surfactant) | 0.20 | 0.20 | 0.20 | 0.20 | 0.13 | 0.20 | 0.20 | 0.30 | 0.20 |
| | (A)/(C)(×10⁻²) | 1.46 | 1.46 | 1.46 | 1.45 | 1.47 | 1.46 | 1.13 | 1.49 | 1.13 |
| Liquid viscosity aftere low-temperature storage (−5° C.) (mPa · s) | | 24 | 25 | 17 | 10 | 34 | 38 | 17 | 54 | 12 |
| Foam viscosity upon discharging from container (mPa · s) | | 6230 | 5715 | 4993 | 4482 | 6035 | 6412 | 4311 | 5530 | 3012 |
| Low-temperature stability (−5° C.) | | A | A | A | A | A | A | A | A | A |

| | | Ex. 27 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|
| (a-1) | Sodium lauryl sulfate | 1 | 0.5 | 0.5 | 0.5 | 0.5 | 0.2 | 1.5 |
| (a-2) | Coconut oil fatty acid amide propyl betaine*³ | 1 | 0.5 | 0.5 | 0.5 | 0.5 | 0.2 | 0.5 |
| (B) | Glycerin | 20 | 20 | 20 | 20 | | | 20 |
| | Propylene glycol | 10 | 10 | 10 | 10 | 5 | 10 | 10 |
| Binder | (ι-) Carrageenan*⁵ | 0.1 | 0.1 | 0.2 | 0.1 | | | 0.1 |
| | Sodium carboxymethylcellulose*⁶ | 0.05 | 0.05 | 0.2 | 0.05 | | | 0.05 |
| | Hydroxyethylcellulose*⁷ | | | | | | | |
| Nonionic surfactant | Polyoxyethylene hardened castor oil (E.O. 40) | | | | | 2 | | |
| | Cetylpyridinium chloride | 0.01 | 0.01 | 0.01 | 0.01 | 0.01 | 0.01 | 0.01 |
| (X) | Perfume | 0.6 | 0.2 | 0.2 | 0.4 | 0.2 | 0.5 | 0.2 |
| | Saccharine sodium | 0.03 | 0.03 | 0.03 | 0.03 | 0.03 | 0.03 | 0.03 |
| | Ethanol | | 10 | | | | | |
| (C) | Water | 67.21 | 58.61 | 68.36 | 66.41 | 93.76 | 89.06 | 67.61 |
| Total | | 100 | 100 | 100 | 100 | 100 | 100 | 100 |
| | (a-2)/(a-1) | 1 | 1 | 1 | 1 | 1 | 1 | 0.33 |
| | Ethanol/(a-1) | — | 20 | — | — | — | — | — |
| | Total of binder | 0.15 | 0.15 | 0.4 | 0.15 | 0 | 0 | 0.15 |
| | Total of component (B) | 30 | 30 | 30 | 30 | 5 | 10 | 30 |
| | Total of component (A) ((a-1) + (a-2)) | 2 | 1 | 1 | 1 | 1 | 0.4 | 2 |
| | (X)/((A) + Nonionic surfactant) | 0.30 | 0.20 | 0.20 | 0.13 | 0.20 | 1.25 | 0.10 |
| | (A)/(C)(×10⁻²) | 2.98 | 1.71 | 1.46 | 1.51 | 1.07 | 0.45 | 2.96 |
| Liquid viscosity aftere low-temperature storage (−5° C.) (mPa · s) | | 65 | 133 | 851 | 48 | 86 | 4 | — |
| Foam viscosity upon discharging from container (mPa · s) | | 5685 | 7757 | 5605 | 6517 | 7706 | 1045 | 7383 |
| Low-temperature stability (−5° C.) | | A | D | A | B | B | C | D |

*³,*⁵,*⁶Same as in Table 1
*⁷SE600 (Daicel Finechem Ltd.)

TABLE 3

| | | Example 28 | Example 29 | Example 30 | Example 31 | Example 32 |
|---|---|---|---|---|---|---|
| (a-1) | Sodium lauryl sulfate | 0.5 | 0.5 | 0.5 | 0.5 | 0.5 |
| (a-2) | Coconut oil fatty acid amide propyl betaine*³ | 0.5 | 0.5 | 0.5 | 0.5 | 0.5 |
| (B) | Glycerin | 10 | 10 | 20 | 20 | 20 |
| | Propylene glycol | 10 | 10 | 15 | 17 | 10 |
| | 1,3-Butylene glycol | 10 | | | | |
| | Polyethylene glycol (PEG6000) | | 5 | | | |
| Binder | (ι-) Carrageenan*⁵ | 0.1 | 0.1 | 0.1 | 0.1 | 0.1 |
| | Sodium carboxymethylcellulose*⁶ | 0.05 | 0.05 | 0.05 | 0.05 | 0.05 |
| | Hydroxyethylcellulose*⁷ | | | | | |
| Nonionic surfactant | Polyoxyethylene hardened castor oil (E.O. 40) | | | | | |
| | Cetylpyridinium chloride | 0.01 | 0.01 | | 0.01 | |
| | Isopropylmethylphenol | | | 0.05 | | 0.02 |

TABLE 3-continued

|   |   | Example 28 | Example 29 | Example 30 | Example 31 | Example 32 |
|---|---|---|---|---|---|---|
| (X) | Perfume | 0.2 | 0.2 | 0.2 | 0.2 | 0.2 |
|  | Saccharine sodium | 0.03 | 0.03 | 0.03 | 0.03 | 0.03 |
|  | Erythritol |  |  |  |  |  |
| (C) | Water | 68.61 | 73.61 | 63.57 | 61.61 | 68.60 |
| Total |  | 100 | 100 | 100 | 100 | 100 |
|  | (a-2)/(a-1) | 1 | 1 | 1 | 1 | 1 |
|  | Ethanol/(a-1) | — | — | — | — | — |
|  | Total of binder | 0.15 | 0.15 | 0.15 | 0.15 | 0.15 |
|  | Total of component (B) | 30 | 25 | 35 | 37 | 30 |
|  | Total of component (A) ((a-1) + (a-2)) | 1 | 1 | 1 | 1 | 1 |
|  | (X)/((A) + Nonionic surfactant) | 0.20 | 0.20 | 0.20 | 0.20 | 0.20 |
|  | (A)/(C)(×10$^{-2}$) | 1.46 | 1.36 | 1.57 | 1.62 | 1.46 |
| Liquid viscosity after low-temperature storage (−5° C.) (mPa · s) |  | 46.9 | 54.6 | 57.6 | 83.1 | 34.4 |
| Foam viscosity upon discharging from container (mPa · s) |  | 5852 | 6150 | 5243 | 6326 | 6520 |
| Low-temperature stability (−5° C.) |  | A | A | a | a | A |

*[3],*[5],*[6]Same as in Table 1
*[7]Same as in Table 2

TABLE 4

|   |   | Example 28 | Example 29 | Example 30 | Example 33 | Example 34 | Comparative Example 7 |
|---|---|---|---|---|---|---|---|
| (a-1) | Sodium lauryl sulfate | 0.5 | 0.5 | 0.5 | 0.5 | 0.5 | 0.5 |
| (a-2) | Coconut oil fatty acid amide propyl betaine*[3] | 0.5 | 0.5 | 0.5 | 0.5 | 0.5 | 0.5 |
| (B) | Glycerin | 10 | 10 | 20 | 20 | 20 | 20 |
|  | Propylene glycol | 10 | 10 | 15 | 10 | 10 |  |
|  | 1,3-Butylene glycol | 10 |  |  |  |  |  |
|  | Polyethylene glycol (PEG6000) |  | 5 |  |  |  | 10 |
| Binder | (ι-) Carrageenan*[5] | 0.1 | 0.1 | 0.1 |  |  | 0.1 |
|  | Sodium carboxymethylcellulose*[6] | 0.05 | 0.05 | 0.05 |  |  | 0.05 |
|  | Hydroxyethylcellulose*[7] |  |  |  | 0.1 | 0.1 |  |
| Nonionic surfactant | Polyoxyethylene hardened castor oil (E.O. 40) |  |  |  |  |  | 1 |
|  | Cetylpyridinium chloride | 0.01 | 0.01 |  | 0.05 | 0.01 | 0.01 |
|  | Isopropylmethylphenol |  |  | 0.05 |  |  |  |
| (X) | Perfume | 0.2 | 0.2 | 0.2 | 0.2 | 0.2 | 0.6 |
|  | Saccharine sodium | 0.03 | 0.03 | 0.03 | 0.03 | 0.03 | 0.03 |
|  | Erythritol |  |  |  | 1 | 3 | 10 |
| (C) | Water | 68.61 | 73.61 | 63.57 | 67.62 | 65.66 | 57.21 |
| Total |  | 100 | 100 | 100 | 100 | 100 | 100 |
|  | (a-2)/(a-1) | 1 | 1 | 1 | 1 | 1 | 1 |
|  | Ethanol/(a-1) | — | — | — | — | — | — |
|  | Total of binder | 0.15 | 0.15 | 0.15 | 0.1 | 0.1 | 0.15 |
|  | Total of component (B) | 30 | 25 | 35 | 30 | 30 | 30 |
|  | Total of component (A) ((a-1) + (a-2)) | 1 | 1 | 1 | 1 | 1 | 1 |
|  | (X)/((A) + Nonionic surfactant) | 0.20 | 0.20 | 0.20 | 0.20 | 0.20 | 0.30 |
|  | (A)/(C)(×10$^{-2}$) | 1.46 | 1.36 | 1.57 | 1.48 | 1.52 | 1.75 |
| Liquid viscosity after low-temperature storage (−5° C.) (mPa · s) |  | 46.9 | 54.6 | 57.6 | 24.0 | 22.5 | 116.9 |
| Liquid viscosity at room temperature (25° C.) (mPa · s) |  | 22.6 | 36.6 | 32.5 | 26.6 | 25.5 | 45.9 |
| Foam viscosity upon discharging from container (mPa · s) |  | 5852 | 6150 | 5243 | 4327 | 4756 | 4727 |
| Low-temperature stability (−5° C.) |  | A | A | a | A | A | A |
| State of discharge port after high-temperature storage |  | A | A | A | A | A | B |
| Foam quality upon discharging at room temperature (25° C.) |  | A | A | A | B | B | C |

*[3],*[5],*[6]Same as in Table 1
*[7]Same as in Table 2

TABLE 5

|  |  | Example 1 | Example 2 | Example 3 | Example 4 | Example 7 | Example 17 | Example 19 |
|---|---|---|---|---|---|---|---|---|
| Cationic bactericide | Cetylpyridinium chloride | 0.01 |  | 0.01 | 0.01 | 0.01 | 0.01 | 0.01 |
|  | Benzethonium chloride |  | 0.01 |  |  |  |  |  |
| (a-1) | Sodium lauryl sulfate | 0.5 | 0.5 | 0.5 | 0.5 | 0.5 | 0.5 | 0.5 |
| (a-2) | Coconut oil fatty acid amide propyl betaine*[3] | 0.5 | 0.5 | 0.5 | 0.5 | 1 | 0.5 | 0.5 |
| (B) | Glycerin | 20 | 20 | 10 | 10 | 20 | 20 | 20 |
|  | Propylene glycol | 10 | 10 | 10 |  | 10 | 10 | 10 |
| Binder | (ι-) Carrageenan*[5] | 0.1 | 0.1 | 0.1 | 0.1 | 0.1 | 0.1 |  |
|  | Sodium carboxymethylcellulose*[6] | 0.05 | 0.05 | 0.05 | 0.05 | 0.05 | 0.02 | 0.1 |
| (X) | Perfume | 0.2 | 0.2 | 0.2 | 0.2 | 0.2 | 0.2 | 0.2 |
|  | Saccharine sodium | 0.03 | 0.03 | 0.03 | 0.03 | 0.03 | 0.03 | 0.03 |
| (C) | Water | 68.61 | 68.61 | 78.61 | 88.61 | 68.11 | 68.64 | 68.66 |
| Total |  | 100 | 100 | 100 | 100 | 100 | 100 | 100 |
|  | (a-2)/(a-1) | 1 | 1 | 1 | 1 | 2 | 1 | 1 |
|  | Total of binder | 0.15 | 0.15 | 0.15 | 0.15 | 0.15 | 0.12 | 0.1 |
|  | Total of component (B) | 30 | 30 | 20 | 10 | 30 | 30 | 30 |
|  | Total of component (A) ((a-1) + (a-2)) | 1 | 1 | 1 | 1 | 1.5 | 1 | 1 |
|  | (A)/(C)(×10$^{-2}$) | 1.46 | 1.46 | 1.27 | 1.13 | 2.20 | 1.46 | 1.46 |
| Foam viscosity upon discharging from container (mPa·s) |  | 6093 | 5896 | 5499 | 4324 | 6493 | 6073 | 5715 |
| Amount of foam medicinal component adsorbed (ng/cm$^2$) |  | 109 | 628 | 63 | 85 | 60 | 63 | 43 |
| Amount of liquid medicinal component adsorbed (ng/cm$^2$) |  | 42 | 472 | 36 | 28 | 52 | 26 | 33 |
| Ratio of amounts of foam/liquid medicinal components adsorbed |  | 2.6 | 1.3 | 1.8 | 3.0 | 1.2 | 2.4 | 1.3 |

*[3],*[5],*[6]Same as in Table 1

TABLE 6

|  |  | Example 35 | Example 36 | Comparative Example 8 | Comparative Example 9 |
|---|---|---|---|---|---|
|  | Triclosan | 0.02 |  | 0.02 |  |
|  | Dipotassium glycyrrhizinate |  | 0.05 |  | 0.05 |
| (a-1) | Sodium lauryl sulfate | 0.5 | 0.5 | 0.5 | 0.5 |
| (a-2) | Coconut oil fatty acid amide propyl betaine*[3] | 0.5 | 0.5 | 0.5 | 0.5 |
| (B) | Glycerin | 20 | 20 | 20 | 20 |
|  | Propylene glycol | 10 | 10 | 10 | 10 |
| Binder | (ι-) Carrageenan*[5] | 0.1 | 0.1 | 0.1 | 0.1 |
|  | Sodium carboxymethylcellulose*[6] | 0.05 | 0.05 | 0.05 | 0.05 |
| Nonionic surfactant | Polyoxyethylene hardened castor oil (E.O.40) |  |  | 2 | 2 |
| (X) | Perfume | 0.2 | 0.2 | 0.2 | 0.2 |
|  | Saccharine sodium | 0.03 | 0.03 | 0.03 | 0.03 |
| (C) | Water | 68.60 | 68.57 | 66.60 | 66.57 |
| Total |  | 100 | 100 | 100 | 100 |
|  | (a-2)/(a-1) | 1 | 1 | 1 | 1 |
|  | Total of binder | 0.15 | 0.15 | 0.15 | 0.15 |
|  | Total of component (B) | 30 | 30 | 30 | 30 |
|  | Total of component (A) ((a-1) + (a-2)) | 1 | 1 | 1 | 1 |
|  | (X)/((A) + Nonionic surfactant) | 0.20 | 0.20 | 0.07 | 0.07 |
|  | (A)/(C)(×10$^{-2}$) | 1.46 | 1.46 | 1.50 | 1.50 |
| Liquid viscosity after low-temperature storage (−5° C.) (mPa·s) |  | 34 | 40 | 47 | 51 |
| Foam viscosity upon discharging from container (mPa·s) |  | 6520 | 6452 | 6142 | 6774 |
| Low-temperature stability (−5° C.) |  | A | A | B | B |
| Amount of foam medicinal component adsorbed (ng/cm$^2$) |  | 105 | 114 | 58 | 83 |

*[3],*[5],*[6]Same as in Table 1

As shown in the results in Tables 1 to 4, it can be seen that the foam viscosity upon discharging from the container was high, the foam quality was good, the storage stability at a low temperature and the dischargeability from the container at a low temperature or the dischargeability after high-temperature storage were excellent in all of Examples 1 to 34, as compared with those in Comparative Example 1 where the content of ethanol was more than 3 mass %, Comparative Example 2 where the content of the binder was more than 0.3 mass %, Comparative Example 3 where the content of the nonionic surfactant was more than 1.2 mass %, Comparative Example 4 where the content of the component (B) was less than 10 mass %, Comparative Example 5 where the content of the component (a-2) was less than 0.25 mass % while the component (a-1) was contained, Comparative Example 6 where the content of the component (a-1) was more than 1.2 mass %, and Comparative Example 7 where the content of the sugar alcohol which is a solid at 20° C. was more than 5 mass %.

In addition, as shown in the results in Tables 5 to 6, it can be seen that, while good foam quality, and excellent storage stability at a low temperature and excellent dischargeability from the container were retained, high adsorption, in the oral cavity, of various medicinal components, were exhibited in all of Examples.

The invention claimed is:

1. A method for enhancing adsorption of one or more bactericides, the method comprising: applying a foam liquid composition in the oral cavity of a subject in need thereof, wherein:
    the one or more bactericides is selected from the group consisting of a cationic bactericide, triclosan, and isopropylmethylphenol; and
    the foam liquid composition comprises:
    (A) 0.3 mass % or more and 2.5 mass % or less in total of one or more surfactants selected from the group consisting of an amphoteric surfactant (a-2) and an anionic surfactant (a-1), wherein the component (a-1) is at least one selected from the group consisting of an N-acylamino acid salt, an alkyl sulfate ester salt, an alkyl phosphate salt and an α-olefin sulfonate salt;
    (B) 10 mass % or more and 40 mass % or less in total of one or more polyols selected from the group consisting of glycerin, propylene glycol, butylene glycol, and polyethylene glycol having an average molecular weight of 1,000 or less; and
    (C) 50 mass % or more and 89 mass % or less of water;
    wherein a content of the component (a-1), if present, is 1.2 mass % or less, and a content of the component (a-2), if present, is 0.25mass % or more and 1.5 mass % or less, and
    wherein a content of ethanol, if present, is 3 mass % or less, a content of an abrasive powder, if present, is 0.5 mass % or less, a content of a binder, if present, is 0.3 mass % or less, a content of a nonionic surfactant, if present, is 1.2 mass % or less, and a content of a sugar alcohol, which is a solid at 20° C., if present, is 5 mass % or less.

2. The method of claim 1, wherein the component (a-1) is present, and the content of the component (a-1) is 0.1mass % or more and 1.2 mass % or less.

3. The method of claim 1, wherein the foam liquid composition further comprises 0.005 mass % or more and 0.1 mass % or less of a cationic bactericide.

4. The method of claim 1, wherein the foam liquid composition further comprises one or more selected from the group consisting of isopropylmethylphenol, triclosan, and glycyrrhizic acid or a salt thereof.

5. The method of claim 1, wherein the foam liquid composition further comprises an oily component (X) which is an oily component other than the component (A), other than the nonionic surfactant, other than isopropylmethylphenol, other than triclosan, and other than glycyrrhizic acid, wherein a mass ratio of the component (X) to a total content of the component (A) and the nonionic surfactant, if present, (X)/((A)+nonionic surfactant), is 0.05 or more and 5 or less.

6. The method of claim 1, wherein a mass ratio of the component (A) to the component (C), (A)/(C), is $0.5 \times 10^{-2}$ or more and $5 \times 10^{-2}$ or less.

7. The method of claim 1, wherein both the component (a-1) and the component (a-2) are present, and a mass ratio of the component (a-2) to the component (a-1), (a-2)/(a-1), is 0.5 or more and 3 or less.

8. The method of claim 1, wherein the component (a-2) is one or more selected from the group consisting of coconut oil fatty acid amide alkyl betaine and alkyl sulfobetaine.

9. The method of claim 5, wherein a content of the component (X) is 0.1 mass % or more and 2 mass % or less.

10. The method of claim 1, wherein prior to the applying, the foam liquid composition is contained in a foam-discharging container that is a non-aerosol container selected from the group consisting of a squeeze container or a pump container provided with a discharge port.

\* \* \* \* \*

UNITED STATES PATENT AND TRADEMARK OFFICE
CERTIFICATE OF CORRECTION

PATENT NO. : 10,524,989 B2
APPLICATION NO. : 15/539914
DATED : January 7, 2020
INVENTOR(S) : Aya Ogihara Page 1 of 1

It is certified that error appears in the above-identified patent and that said Letters Patent is hereby corrected as shown below:

On the Title Page

Item (87), the PCT Publication number is incorrect. Item (87) should read:
-- (87)  PCT Pub. No: WO2016/104730
         PCT Pub. Date: Jun. 30, 2016 --

Signed and Sealed this
Eighteenth Day of February, 2020

Andrei Iancu
*Director of the United States Patent and Trademark Office*